United States Patent
McHale (12) 
(10) Patent No.: US 6,495,351 B2
(45) Date of Patent: Dec. 17, 2002

(54) LOADING SYSTEM AND METHOD FOR USING THE SAME

(75) Inventor: Anthony Patrick McHale, Londonderry (IE)

(73) Assignee: Gendel Limited, Coleraine (GB)

( * ) Notice: Subject to any disclaimer, the term of this patent is extended or adjusted under 35 U.S.C. 154(b) by 85 days.

(21) Appl. No.: 09/779,186

(22) Filed: Feb. 8, 2001

(65) Prior Publication Data

US 2001/0031499 A1 Oct. 18, 2001

Related U.S. Application Data

(63) Continuation of application No. 09/748,789, filed on Dec. 22, 2000, and a continuation of application No. 09/748,063, filed on Dec. 22, 2000.
(60) Provisional application No. 60/181,796, filed on Feb. 11, 2000.
(51) Int. Cl.⁷ .................................. C12N 13/00
(52) U.S. Cl. ................ 435/173.6; 435/173.7; 435/294.1; 435/292.2; 435/306.1
(58) Field of Search .................. 435/173.6, 173.7, 435/294.1, 292.2, 306.1

(56) References Cited

U.S. PATENT DOCUMENTS

2002/0006378 A1 * 1/2002 Young et al. ............... 424/1.11

* cited by examiner

*Primary Examiner*—James Ketter
(74) *Attorney, Agent, or Firm*—Palmer & Dodge LLP; Kathleen M. Williams (57) ABSTRACT

A loading system for providing a cell suitable for delivery of an agent to a vertebrate, the system comprise a loading module for loading a cell with an agent; and a sensitisation module in fluid communication with the loading module, the sensitisation module for sensitising a cell to an energy field, such that said cell is induced to release the agent upon exposure to said energy field. The system can be used to transform a cell, such as a red blood cell, into a delivery vehicle for delivering a therapeutic agent and/or an imaging agent to a vertebrate, and in particular, to a mammal, such as a human being.

21 Claims, 4 Drawing Sheets

LOADING SYSTEM AND METHOD FOR USING THE SAME

RELATED APPLICATIONS

This application is a continuation of U.S. patent application Ser. No. of 09/748,063, and U.S. patent application Ser. No. 09/748,789, both filed Dec. 22, 2000, and under 35 U.S.C. §119(e) to U.S. Provisional Application No. 60/181,796, filed Feb. 11, 2000. This application also claims priority under 35 U.S.C. §119(a)–(d) to GB 0002856.2, filed Feb. 8, 2000. The entireties of these applications are incorporated by reference herein.

FIELD OF THE INVENTION

This invention relates to the field of medical devices. In particular, the invention relates to a system for rendering a delivery vehicle suitable for delivery of an agent to a vertebrate, and a method of using the same.

BACKGROUND

The delivery of therapeutic agents to specific tissues is desirable to ensure that a sufficiently high dose of a given agent is delivered to a selected tissue while avoiding undesirable side effects in tissues that are not diseased. For example, in the treatment of cancer, it is necessary to use a high enough dose of a drug to kill abnormally proliferating cells without killing an unacceptably high number of normal cells. Thus, one of the major challenges of disease treatment is to identify ways of using cellular drug delivery vehicles to incorporate and to selectively release agents at a desired target site.

It has been suggested that red blood cells (RBCs) may be exploited as active agent/drug delivery vehicles (DeLoach & Sprandel 1985, *Bibliotheca Haematologica;* Publ. Karger, Munich) since it is possible to incorporate agents into human RBCs using a variety of loading techniques. An example of a loading technique is electroporation. During electroporation, red blood cell membranes are made transiently permeable by exposing the membranes to short pulses of high electric fields, thereby allowing agents of interest to enter the cells. The electroporation process allows high loading indices to be achieved within a very short time period (Flynn et al., 1994, *Cancer Letts.,* 82, 225–229).

Loading of cells after osmotic shock followed by a recovery period to allow cells to recover isotonicity, and loading after hypotonic shock, followed by reverse hypotonic dialysis has also been performed (see, e.g., Luque & Pinilla, 1993, *Ind Farmac.* 8, 53–59).

SUMMARY

The present invention provides a system for rendering a cell, such as a red blood cell, suitable for use as a delivery vehicle for delivering an agent (e.g., a drug) to a vertebrate.

The invention provides a loading system for loading a cell with an agent and for sensitising a cell to an energy field, thereby allowing a cell to release its contents, including the agent, in response to the energy field.

In one embodiment, the system comprises: a loading module for loading a cell with an agent; and a sensitisation module in fluid communication with the loading module, the sensitisation module for sensitising a cell to an energy field, such that the cell is induced to release the agent upon exposure to the energy field, and wherein the sensitisation module and the loading module are separate.

In one embodiment, the loading module comprises a mechanism for loading the cell by hypotonic dialysis.

In another embodiment, the loading module comprises one or more hollow fibers.

In a further embodiment, the system comprises a pre-sensitisation module for exposing a cell to a condition which increases the ability of a cell to be loaded in the loading module at least two-fold compared to a cell which is not pre-sensitised. In one embodiment, the presensitisation module and the sensitisation module are integral. In another embodiment, the presensitisation module and the sensitisation module are separate and are in fluid connection with each other.

In one embodiment, one or both of the sensitisation module and the pre-sensitisation module are in communication with a source of electrical energy.

In another embodiment, the sensitisation module comprises a chamber for receiving at least one cell, one or more walls of the chamber being defined by electrodes to enable an electric field to be established within the chamber. In one embodiment, at least one electrode has a crenellated or sinusoidal cross sectional profile. In another embodiment, the sensitisation module comprises one or more flow-through cuvettes. In still another embodiment, the sensitisation module comprises one or more micropores. In a further embodiment, the micropore comprise electrodes positioned to define a space capable of allowing passage of a cell. In one embodiment, the cell is a red blood cell. In another embodiment, the electrodes are tubular.

In one embodiment, the system further comprises a resealing module for resealing the cell subsequent to loading. In another embodiment, the system further comprises a monitoring module comprising a sensor for sensing the amount of agent which is loaded into the red blood cell. In a further embodiment, the system comprises a feedback mechanism adapted to receive a signal from the monitoring module and to alter one or more loading parameters to adjust the amount of agent loaded into the cell.

As described above, the system comprises a plurality of modules. The modules can be configured and/or operated in a number of different ways:

In a first embodiment of the invention, the system comprises a sensitisation module (S) and a loading module (L). The sensitisation module and loading module are in fluid connection with each other. The sensitisation module acts on cells to sensitize the cells such that the cells undergo lysis upon the subsequent application of an energy field such as ultrasound. The loading module enables the cells to be loaded with an agent of interest. The sensitisation module may be placed before or after the loading module, such that the cells are sensitised and subsequently loaded, or loaded and subsequently sensitised. In a preferred embodiment, the cells which are loaded are red blood cells.

In a second embodiment of the invention, the system comprises a pre-sensitisation module (P), a sensitisation module (S) and a loading module (L). The modules are in fluid connection with each other. The sensitisation and loading modules act on the cells, as described above and therefore may be connected to each other in any order. The pre-sensitisation module enables the cells to be pre-sensitised so that the cells will subsequently undergo efficient loading, and must therefore be placed before the loading module. The modules may therefore be connected in the following order: S, P, L; P, S, L; and P, L, S.

In a third embodiment of the invention, the system comprises a pre-sensitisation module and a loading module in fluid connection with each other. As noted above, the pre-sensitisation module acts on cells so that the cells will subsequently undergo efficient loading, and thus, this module is placed before the loading module. In a preferred embodiment, the cells are red blood cells.

In a fourth embodiment, the system comprises a pre-sensitisation/sensitisation module (referred to here as a "bifunctional module") and a loading module in fluid connection with each other. In this embodiment a single module is used to enable pre-sensitisation and sensitisation of cells. A number of ways of configuring the modules are available in this embodiment. In one option, the cells pass into the bifunctional module first for pre-sensitisation and then into the loading module for loading. After passing through the loading module, the cells pass back into the bifunctional module for a second time, where sensitisation of the cells takes place. In a preferred embodiment, the cells are red blood cells.

A further option is to pass the cells into the bifunctional module for pre-sensitisation, then back through the bifunctional module for a second time for sensitisation. After exiting the bifunctional module for a second time the cells are then fed into the loading module for loading. The bifunctional module therefore acts to pre-sensitise the cells on the first pass and sensitise the cell on the second pass. The reverse configuration may also be used, in which the bifunctional module sensitises the cells the first time, and pre-sensitises the cells the second time. The cells are then loaded with agent in the loading module. In a preferred embodiment, the cells are red blood cells.

The loading systems described above may include additional modules such as an optional washing module, and/or an optional resealing module. Thus, one or both of the washing and resealing modules may be included in any of the configurations described above. These may be placed after the loading modules. Further resealing and/or washing modules may also be placed after the pre-sensitisation and sensitisation modules. Monitoring modules may also be used in any of the above-described combinations and in any positions in the system.

The invention further provides a method for providing a cell suitable for delivery of an agent to a vertebrate, the method comprising the steps of: (a) providing an system according to the first embodiment of the invention; (b) loading the cell with an agent in the loading module of the system according to the first embodiment of the invention; and (c) sensitising the cell in the sensitising means of the system. In a preferred embodiment, the method is used to transform a red blood cell into a delivery vehicle for an agent.

In another embodiment, the method comprises the steps of: (a) providing a system according to the second embodiment of the invention; (b) loading the cell with an agent in the loading module of the system; and (c) pre-sensitising the cell in the pre-sensitising means of the system. In a preferred embodiment, the method is used to transform a red blood cell into a delivery vehicle for an agent.

In a further embodiment, the method comprises the use of an electroporation system for the sensitisation, or the pre-sensitisation of a cell, such as a red blood cell.

BRIEF DESCRIPTION OF THE DRAWINGS

The invention will now be described by means of a description of various preferred nonlimiting embodiments, with reference to the Figures, in which.

DETAILED DESCRIPTION

Energy fields, such as electric fields, can be used to sensitise a cell to ultrasound. Thus, exposing a sensitised cell to ultrasound will cause it to unload its contents while surrounding cells are only minimally effected. By loading a cell with a therapeutic agent, prior to, or after sensitisation, the cell becomes an efficient delivery vehicle for agents such as drugs. PCT/GB00/02848 and PCT/GB00/03056, the entireties of which are incorporated by reference herein, both describe the use of such a technique to deliver sensitised red blood cells carrying agents to a vertebrate, such as a human being. The present invention provides a loading system for transforming a cell, such as a red blood cell, into a delivery vehicle for a variety of agents, such as imaging agents, therapeutic agents, and the like. In one embodiment, the loading system comprises a plurality of modules, one or more of which are in fluid communication with each other, to perform sensitisation and loading procedures.

DEFINITIONS

In order to more clearly and concisely describe and point out the subject matter of the claimed invention, the following definitions are provided for specific terms which are used in the following written description and the appended claims.

The term "sampling" as used herein refers to the collection of a source of cells (e.g., red blood cells) and the subsequent processing of that source to produce a solution of cells suitable for further processing steps (e.g., pre-sensitisation, sensitisation, loading, etc).

The term "sampling module" is to be understood to be any device that can perform "sampling" such as described further below.

A "sampling procedure" is an event, or events, that occur in the sampling module to achieve sampling of cells.

The term "in fluid connection with" or in "fluid communication with" as used herein refers to the ability of fluid to pass from one module to another either continuously or discontinuously.

As used herein, the term "loading" refers to introducing into a cell, such as a red blood cell, at least one agent. In a preferred embodiment, the agent is loaded by becoming internalised into the cell. Loading of a cell with more than one agent may be performed such that the agents are loaded individually (in sequence) or together (simultaneously or concurrently). Loading is generally performed in a separate procedure than sensitising. Agents may be first admixed at the time of contact with the cells or prior to that time.

The term "loading module" is to be understood to be any device that can perform "loading" such as described further below.

A "loading procedure" is an event, or events, that occur in the loading module to achieve loading of cells.

The term "sensitisation" as used herein, refers to the destabilisation of cells without causing fatal damage to the cells. As used herein, "destabilization" refers to an alteration of a membrane of a cell that makes the cell more susceptible to lysis in vitro or in vivo upon exposure to an energy field such as ultrasound. In one embodiment of the invention, a cell which is destabilized is a cell which is lysed when less than 20%, and preferably less than 5%–10%, or less than 1% of non-sensitised cells are lysed. Destabilisation may be achieved by exposing a cell, such as a red blood cell to an energy field, such as an electric field.

The term "electrosenitisation" as used herein refers to the sensitisation of a cell that occurs upon momentary exposure of the cell to one or more pulses of a high electric field. Electrosensitisation typically involves the use of electric fields which do not possess sufficient energy to electroporate cells. Electroporation, which facilitates the passage of agents into a cell without significant loss of cellular contents or cell viability is well known in the art, and apart from the energy levels involved is similar to electrosensitisation. Cells which are electroporated may become electrosensitised, However, as the term is used in the instant application, electrosensitisation is carried out at energy levels insufficient to electroporate a cell and permit the passage of substances through the cell membrane.

The term "sensitisation module" is to be understood to be any device that can perform any form of "sensitisation" such as described further below.

The term "sensitisation procedure" is an event, or events, that occur in a sensitisation module which destabilizes cells without causing fatal damage to the cells.

As used herein, the term "pre-sensitisation" refers to enhancing the efficiency of loading an agent into a cell, such as a red blood cell, compared to a cell which has not been subjected to pre-sensitisation. In one embodiment, loading efficiency is increased at least two-fold, 5-fold, 10-fold, 50-fold, or 100-fold compared to non-pre-sensitised cells. The term "pre-sensitisation" encompasses the destabilisation of cells without causing fatal damage to the cells. As used herein, a pre-sensitisation condition, is any condition to which a cell can be exposed which increases loading efficiency of the cell in comparison to a cell which is not pre-sensitised.

The term "pre-sensitisation module" is to be understood to be any device that can perform any form of "pre-sensitisation" such as described further below.

The term "pre-sensitisation procedure" is an event, or events, that occur in a presensitisation module which destabilizes cells without causing fatal damage to the cells.

As used herein, the term "electric pulse" includes one or more pulses at variable capacitance and voltage and including exponential and/or square wave and/or modulated wave forms.

The term "resealing" encompasses the stabilization of the membrane of a cell by closing pores in the membrane that have previously been opened by some other process, for example, by a loading process such as hypotonic dialysis.

The term "resealing module" is to be understood to be any device that can perform any form of "resealing" is described further below.

A "resealing procedure" is an event or events that occur in a resealing module to reseal cells.

As used herein, the term "placing a cell within a module" or grammatical equivalents thereof, refers to manually placing a cell in a module by pipeting, or pouring using a container, or tubing; however, in one embodiment, "placing" refers to the process of allowing a cell in a solution to flow from one module to another within the system.

As used herein, the term "sensor" refers to any mechanism which can be used to detect a parameter of a fluid within a module of the system.

As used herein, a module which is "integral" with another module is one which is part of another module. As used herein, a module which is "separate" from another module is one which is not a part of another module. A cell which is exposed to a procedure in separate modules must be moved from one module to another in order to be so exposed, while a cell which is exposed to a procedure in modules which are integral with each other does not need to be moved to be so exposed.

As used herein, the term "agent" includes but is not limited to an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate.

As used herein, an "imaging agent" is an agent which may be detected, whether in vitro or in vivo in the context of a tissue, organ or organism in which the agent is located.

As used herein, the term "biological effector molecule" or "biologically active molecule" refers to an agent that has activity in a biological system, including, but not limited to, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanised, a peptide hormone, a receptor, and a signalling molecule. Included within the term "immunoglobulin" are intact immunoglobulins as well as antibody fragments such as Fv, a single chain Fv (scFv), a Fab or a F(ab')$_2$.

As used herein, the term "target site" is the site to which the delivery vehicle or cell loaded with a biological effector molecule will be delivered.

Loading Module

In one embodiment, the loading system according to the invention comprises a loading module for bringing a cell, such as a red blood cell, in contact with an agent to be loaded and for exposing a cell to conditions under which it will take up the agent. According to a preferred embodiment of the invention, a loading module comprises a vessel or chamber allowing mixing of cells with a buffer solution comprising the agent to be loaded. Preferably, the loading module is in a form which allows rapid exchange of cells with agents to be loaded.

Loading may be performed by a procedure selected from the group consisting of: iontophoresis, electroporation, sonoporation, microinjection, calcium precipitation, membrane intercalation, microparticle bombardment, lipid-mediated transfection, viral infection, osmosis, dialysis, including hypotonic dialysis, osmotic pulsing, osmotic shock, diffusion, endocytosis, phagocytosis, crosslinking to a cell surface component (e.g., a red blood cell surface component), chemical crosslinking, mechanical perforation/ restoration of the plasma membrane by shearing, single-cell injection, or a combination thereof.

Sonoporation as a method for loading an agent into a cell is disclosed in, for example, Miller, et al (1998), *Ultrasonics* 36, 947–952, the entirety of which is incorporated by reference herein.

Iontophoresis uses an electrical current to activate and to modulate the diffusion of a charged molecule across a biological membrane, such as the skin, in a manner similar to passive diffusion under a concentration gradient, but at a facilitated rate. In general, iontophoresis technology uses an electrical potential or current across a semipermeable barrier. By way of example, delivery of heparin molecules to patients has been shown using iontophoresis, a technique which uses low current (i.e., D.C.) to drive charged species into the arterial wall. The iontophoresis technology and references relating thereto is disclosed in WO 97/49450, the entirety of which is incorporated by reference herein.

In a preferred embodiment of the invention, loading takes place by way of hypotonic dialysis. Thus, in a preferred embodiment the loading module comprises one or more dialysis devices. The dialysis devices used may be conventional dialysis devices as known in the art. Dialysis devices work on the principle of osmotic shock, whereby loading of an agent into a cell, such as a red blood cell, is facilitated by the induction of sequential hypotonicity and recovery of isotonicity. The term "osmotic shock" is intended herein to be synonymous with the term "hypotonic dialysis" or "hypoosmotic dialysis." An exemplary osmotic shock/hypotonic dialysis method is described in Eichler, et al., 1986, Res. Exp. Med. 186: 407–412, the entirety of which is incorporated by reference herein.

For example, in one embodiment, washed red blood cells are suspended in 1 ml of PBS (150 mM NaCl, 5 mM $K_2HPO_4/KH_2PO_4$; pH 7.4) to obtain a hematocrit of approximately 60%. The suspension is placed in dialysis tubing (molecular weight cut-off 12–14,000; Spectra-Por) and cells are dialyzed against 100 ml of 5 mM $K_2HPO_4/KH_2PO_4$, pH 7.4 for 90 minutes at 4° C., thereby swelling the cells and rendering them permeable to agents to be loaded. Resealing is achieved by further dialysis, e.g., for 15 minutes at 37° C. against 100 ml of PBS containing 10 mM glucose. Cells are then washed in ice cold PBS containing 10 mM glucose using centrifugation.

In other embodiments, the loading module implements other osmotic shock procedures such as described, for example, in U.S. Pat. No. 4,478,824, the entirety of which is incorporated by reference herein. In these embodiments, a packed red blood cell fraction is incubated in a solution containing a compound (such as dimethyl sulphoxide (DMSO) or glycerol) which readily diffuses into and out of cells. The compound rapidly creates a transmembrane osmotic gradient by diluting the suspension of red blood cells in the solution with a near-isotonic aqueous medium. By including an anionic agent in the medium which may be an allosteric effector of haemoglobin, such as inosine monophosphate or a phosphorylated inositol (e.g., inositol hexaphosphate), water diffuses into the cells, swelling the cells and increasing the permeability of the outer membranes of the cells. Thus, the method may be used to load cells with anionic agents, as the increase in the cells' permeability is maintained for a period of time sufficient only to permit transport of the anionic agent into the cells and diffusion of readily-diffusing compounds out of the cells. However, this is not the method of choice where the desired agent to be loaded into cells is not anionic, or is anionic or polyanionic, but is not present in the near-isotonic aqueous medium in sufficient concentration to cause the needed increase in cell permeability without cell destruction.

U.S. Pat. No. 4,931,276 and International Application WO 91/16080, the entireties of which are incorporated by reference herein, also disclose methods of loading red blood cells with selected agents using an osmotic shock technique. In one embodiment, the loading system implements these techniques to load red blood cells within the loading module, i.e., by providing an effective amount of an osmotic shocking agent to render cell membranes transiently permeable, enabling the cells to be loaded with the agent. An alternative osmotic shock procedure is described in U.S. Pat. No. 4,931,276, which is incorporated herein by reference, and in one embodiment, the system implements the method described therein.

In another embodiment, the loading module comprises a mechanism for microparticle bombardment of cells, as known in the art. In this embodiment, gold particles are coated with an agent to be loaded, dusting the particles onto a 22 caliber bullet. The bullet is fired into a restraining shield made of a bullet-proof material and having a hole smaller than the diameter of the bullet, such that the gold particles continue in motion toward cells in vitro and, upon contacting these cells, perforate them and deliver the payload (i.e., the agent) to the cell cytoplasm.

It will be appreciated by one skilled in the art that combinations of methods may be used to facilitate the loading of a red blood cell with agents of interest, and that the loading module may comprise mechanisms for accomplishing these methods. Likewise, it will be appreciated that a first and second agent, may be loaded concurrently or sequentially, in either order, into a cell, such as a red blood cell, in the system of the present invention.

Preferably, the loading module comprises a large surface area for equilibration of an agent with the contents of cells. Preferentially, the loading module provides for rapid buffer exchange. In one embodiment, the loading module comprise an element for retaining a cell, such as a red blood cell, while allowing buffer to be drained and replaced. Preferably, the loading module provides multiple chambers that may be used in parallel. Preferably, a plurality of hollow fibers, optionally in the form of a cartridge, is used for loading. The use of hollow fibers facilitates rapid and homogeneous buffer exchange, thereby reducing loading times and providing enhanced control over the loading process. The use of a multiplicity of hollow fibers in the form of cartridges further enables the system to operate in a continuous mode. Additionally, the use of more than one hollow fiber cartridge allows several different agents, or combination of agents, to be loaded simultaneously.

In other embodiments, the loading module comprises a mechanism for agitating or shaking the cells, to speed up the loading process, for example, in an embodiment, where the loading module comprises one or more dialysis elements. Methods of agitation are well known in the art. In additional embodiments, the loading module comprises temperature control elements for maintaining a desired temperature.

In a highly preferred embodiments of the invention, the loading module comprises two or more compartments which are separated by a semi-permeable membrane. Semi-permeable membranes are known in the art, and include cellulose acetate, polyethylene and polypropylene. Thus, in one particular embodiment, the loading module comprises a container or bag with at least one semi-permeable surface, in which cells, such as red blood cells, are retained. Such a container may take the form of a piece of dialysis tubing, which may be restrained at each end by suitable means, for example, clips. The dialysis tubing may be suspended in further container which holds an appropriate buffer or medium. Preferably, the container holding the medium is in a tubular form, for example, a tube or pipe, through which the medium may be passed.

As discussed above, various loading modalities are possible, and a preferred method using hypotonic dialysis is described here. To load red blood cells, red blood cells are placed in an isotonic buffer comprising agent to be loaded within a semipermeable membrane, such as dialysis tubing. The container holding the red blood cells (in this case, the dialysis tubing) is then exposed to a hypotonic environment. Dialysis occurs so that the red blood cells are exposed to gradual decreases in tonicity of the medium, thus forming pores on the their membranes, and allowing an agent to be loaded into the cells. The buffer is then exchanged for a isotonic buffer for resealing the pores. Where the container for containing the cells is a tubular member comprising a semi-permeable membrane, preferably a continuous or semi-continuous flow of medium is maintained. This allows a maximum concentration gradient to exist across the membrane for maximum dialysis efficiency.

In another embodiment, the loading module comprises an inner tubular member disposed within an outer tubular member, one of which carries red blood cells, and other of which carries the relevant medium or buffer (e.g., dialysis buffer). The interface between the cells and the medium or buffer comprises a semi-permeable membrane. Either the cells or the medium, or both, may be in flow. For example, red blood cells may flow in the inner tubular member, while a hypotonic/isotonic buffer flows in the outer tubular member. Dialysis and buffer exchange occurs as described above.

In a further embodiment, the loading module comprises a plurality of hollow fibers, through which medium flows. The hollow fibers are enclosed in a chamber in which cells, such as red blood cells, are suspended. Flow of medium through the hollow fibers allows rapid dialysis and loading of the cells.

The loading module may be of any suitable size, depending on the volume of cells to be sensitised. For example, a loading module may be capable of containing 300 mls of diluted red blood cells. The loading module must be sufficiently sized to load at least one cell.

Sensitisation Module

In some embodiments of the invention, the loading system comprises a sensitisation module, for sensitising cells such as red blood cells. The purpose of sensitisation is to facilitate the release of the contents of the cells at a target site. A sensitised cell will undergo lysis in response to an applied stimulus such as an energy field. An example of a suitable and preferred energy field for disruption of a red blood cell includes, but not limited to, an ultrasound field.

Sensitisation destabilizes cells without causing fatal damage to the cells. This destabilisation may be achieved by applying an energy field to the cells, including, but not limited to, an electric field. In a preferred embodiment of the invention, sensitisation is caused by a momentary exposure of the cells to one or more pulses of high electric field strength (electrosensitisation).

In general, a sensitisation module according to the invention comprises a chamber for receiving at least one cell, such as a red blood cell, which is in communication with an energy source. In one embodiment, a sensitisation module comprises a mechanism for establishing and exposing cells to an electric field. When sensitisation is performed by exposing cells to one or more electrical pulses, the sensitisation chamber may comprise one or more electrodes, which may be an integral part of one or more walls of the chamber. In a preferred embodiment, one or more walls of the chamber are defined by electrodes to enable an electric field to be established within the chamber.

The sensitisation module may take several forms, but preferably comprises one or more flow cells. In one embodiment, the sensitisation module comprises a flow-through cuvette or a micropore. In one embodiment, a flow-through cuvette in the form of a vessel or chamber is provided which comprises one or more pairs of electrodes arranged so that cells, such as red blood cells, may flow between the electrodes. The electrodes impart an electric field on the cells that sensitizes the cells.

The sensitisation module may additionally comprise one or more micropores through which cells flow. Like a flow-through cuvette, the micropore comprises a pair of electrodes arranged so that cells may flow between the electrodes; however, the electrodes in a micropore are separated by a gap which is less than the gap used in conventional flow-through cuvettes. Flow cells, micropores, and the like, may be produced by nanofabrication techniques routine in the art.

The sensitisation module may be optimized to accommodate particular volumes of cells a user desires to sensitize. For example, a sensitisation module may be capable of containing 300 mls of diluted red blood cells. Minimally, a sensitisation module is of a size suitable to sensitize at least one cell, such as a red blood cell.

In one embodiment, the sensitisation module comprises an electroporator. Suitable electroporators include those which are commercially available, such as the Electro Cell Manipulator Model ECM 600R or ECM630, available from Gentronics Inc., of Dan Diego, Calif., U.S.A, or the Gene Pulser I or II, made by Biorad. Other electroporation devices are known in the art.

In one embodiment, the electric field that sensitizes the cells may be produced by a pulse generator included as part of, or in communication with, the sensitiser module Pulse generators used in the invention are preferably those capable of producing different waveforms. Examples of such waveforms include, but are not limited to, multiple pulses, sequential pulses, double pulses, square waves, modulated square waves, exponential waves, sinusoidal waves, a unipolar oscillating pulse train or a bipolar oscillating pulse train. Preferably the application of the electric field is in the form of multiple pulses such as double pulses of the same strength and capacitance or sequential pulses of varying strength and/or capacitance.

The output of the pulse generator may be controlled manually, or by a computer or microprocessor. The computer may be pre-programmed, or may accept instructions from a user. In the case when the computer accepts instructions from a user, it is preferred that the user enters the instructions using menu-driven software via, for example, a touch-sensitive screen. The computer may further include software have a fail-safe routine that does not accept erroneous instructions. The computer system may be an integral part of the system or the system may have a means for linking to an external computer or processor by, for example an RS232 interface or server.

In a preferred aspect of the present invention, the sensitisation module is capable of generating an electric field having a strength of from about 0.1 kV /cm to about 10 kV/cm under in vitro conditions and more preferably from about 1.5 kV/cm to about 4.0 kV/cm under in vitro conditions. Most preferably, the electric field strength is about 3.625 kV/cm under in vitro conditions.

Preferably, the electric field has a strength of from about 0.1 kV/cm to about 10 kV/cm under in vivo conditions (see, as described in WO97/49450, the entirety of which is incorporated by reference herein).

Preferably, the electric field is applied in the form of multiple pulses, such as double pulses of the same strength and capacitance, or sequential pulses of varying strength and/or capacitance. A preferred type of sequential pulsing comprises delivering a pulse of less than 1.5 kV/cm and a capacitance of greater than 5 $\mu$F, followed by a pulse of greater than 2.5 kV/cm and a capacitance of less than 2 $\mu$F, followed by another pulse of less than 1.5 kV/cm and a capacitance of greater than 5 $\mu$F. In one embodiment, sequential pulsing comprises delivering a pulse of 0.75 kV/cm at a capacitance of 10 $\mu$F; followed by a pulse of 3.625 kV/cm, at a capacitance of 1 $\mu$F, followed by another pulse of 0.75 kV/cm at a capacitance of 10 $\mu$F.

Preferably the electric pulse is delivered as a waveform selected from an exponential wave form, a square wave form and a modulated wave form.

In a particularly preferred embodiment, the following electrosensitisation protocol is used. Red blood cells are suspended at a density of $7 \times 10_8$ cells/ml or lower in the sensitisation module and exposed to two electric pulses (field strength=3.625 kV/cm at a capacitance of 1 $\mu$F) using an electrosentising module as described above. Cells are immediately washed with PBS containing $MgCl_2$ (4 mM) (PBS/Mg) and retained at room temperature for at least 30 min in the PBS/Mg$^{++}$ buffer at a concentration of $7 \times 10^8$ cells/ml to facilitate re-sealing. Optionally, cells are subsequently washed and suspended at a concentration of $7 \times 10^8$ cells/ml in PBS/Mg$^{++}$ containing 10 mM glucose (PBS/Mg/glucose) for at least 1 hour.

Pre-sensitisation Module

The pre-sensitisation module enables pre-sensitisation of the red blood cells to be achieved. The purpose of pre-sensitisation is to enhance the efficiency of loading of an agent into a cell, such as a red blood cell, compared to a red blood cell which has not been subjected to pre-sensitisation. Like sensitisation, pre-sensitised cells are destabilized without fatal damage. Pre-sensitisation may take the form of an electrosensitisation step, as described below. Alternatively, or in addition, pre-sensitisation may be effected by the use of ultrasound.

Still other methods may be used to pre-sensitise cells and enhance loading efficiency. For example, electromagnetic radiation such as microwaves, radio waves, gamma rays and X-rays can be used. In another embodiment, chemical agents are used to pre-sensitise cells. Such agents include, but are not limited to, DMSO and pyrrolidinone. In a further embodiment, cells are pre-sensitised by exposure to thermal energy. This may be achieved by raising the temperature of the cells by conventional means, by heat shock, or by the use of microwave irradiation. In general, any method which perturbs or destabilises the surface membrane of a cell, such as a red blood cell (optionally forming pores) can be used to pre-sensitise the cell. Accordingly, a pre-sensitisation module according to the invention is any mechanism for exposing cells to any of the pre-sensitising agents, energy, forms, etc, described above.

In preferred embodiments of the invention, the pre-sensitising module comprises a mechanism for electrosensitising cells, such as red blood cells. The mechanism is used to transiently expose cells to one or more pulses of electricity at high electric field strength, resulting in membrane destabilisation. The strength of the electric field may be adjusted up or down depending upon the resilience or fragility, respectively, of the cells being loaded and the ionic strength of the medium in which the cells are suspended. The electrical parameters that cause efficient pre-sensitisation may be different to the electrical parameters that cause efficient sensitisation.

The pre-sensitisation module may take several forms, but is preferably in the form of one or more flow cells. For example, the pre-sensitisation module may comprise a flow-through cuvette or a micropore. A flow-through cuvette may be in the form of a vessel that comprises one or more pairs of electrodes arranged so that cells, such as red blood cells may flow between the electrodes. The electrodes impart an electric field on the cells that pre-sensitizes the cells. A micropore may also be provided in the form of a vessel through which cells, such as red blood cells, flow and may comprise a pair of electrodes arranged so that cells may flow between the electrodes. However, typically, the electrodes in a micropore are separated by a gap which is less than the gap used in conventional flow-through cuvettes. The flow cell, micropore, etc, may be produced by nanofabrication techniques known in the art.

In the present invention the electric field that pre-sensitizes the cells may also be produced by a pulse generator. The pulse generator is preferably one capable of producing different waveforms, including, but not limited to, multiple pulses, sequential pulses, double pulses, square waves, modulated square waves, exponential waves, sinusoidal waves, a unipolar oscillating pulse train or a bipolar oscillating pulse train. Preferably the application of the electric field is in the form of multiple pulses such as double pulses of the same strength and capacitance or sequential pulses of varying strength and/or capacitance.

The output of the pulse generator may be controlled manually, or by computer or microprocessor. The computer may be pre-programmed, or may accept instructions from a user. In the case when the computer accepts instructions from a user, it is preferred that the user enters the instructions using menu-driven software via for example a touch sensitive screen. The software on the computer may furthermore have a fail-safe routine that does not accept erroneous instructions. The computer system may be an integral part of the system or the system may have a means for linking to an external computer or processor by, for example an RS232 interface, or server.

The pre-sensitisation module may comprise an electroporator as known in the art. Examples of such electroporators include those listed above for the Sensitisation Module.

Sampling Module

In further embodiments, the loading system comprises a sampling module for collecting a source of cells, such as red blood cells, and for processing the source of cells to produce a solution of cells suitable for further processing steps (e.g., pre-sensitisation, sensitisation, and loading, etc). In one embodiment, the source of cells is blood and the cells collected are red blood cells. In another embodiment, the sampling module further processes the red blood cells to produce a buffered solution of red blood cells. In a further embodiment, the processing performed by the sampling instrument comprises the separation of the red blood cells from other components, such as serum, white blood cells, platelets, medium etc. Processing may further comprise the addition of diluents and/or anticoagulants to the source of cells.

Red blood cells may come from any suitable source. In one embodiment, red blood cells are obtained from whole blood or packed red blood cells suspended in a buffer solution. Where the source is whole blood, the sampling module may comprise any device known in the art capable of taking a sample of red blood cells from the body of a patient and separating components of interest from other components.

The plurality of functions provided by the sampling module (e.g., collecting, separating, processing, and the like) may be performed by physically separate elements of the sampling module. For example, in one embodiment, the sampling module comprises a plurality of functionally distinct chambers, e.g., such as one or more of a collecting chamber, separating chamber and/or processing chamber. One or more chambers are fluidly connected to one another, and source fluid can be continuously or discontinuously transferred from one chamber to another (e.g., through a series of valve mechanisms).

In another embodiment, multiple functional elements are provided within single chamber(s) for sequential activation at the appropriate times. In one embodiment, a separating element is provided within a collecting chamber which is selectively activateable by a user (either directly or via a processor in communication with the system) to implement its separating function. For example, in one embodiment, the collecting chamber is provided with a centrifugation mechanism that is activateable by the user when the chamber receives a source fluid comprising red blood cells. Thus the collecting chamber can be selectively turned into a separating chamber by the user at a desired time.

In a further embodiment of the invention, at least a portion of the sampling module (e.g., a collection chamber) comprises an anti-coagulant for facilitating collecting and processing of red blood cells. Anticoagulants encompassed within the scope of the invention include, but are not limited to, CPD, CPDA-1, and heparin. The anticoagulants may be provided in solution, or in a lyophilized form which reconstitutes upon contact with a source of red blood cells (e.g., such as blood). Additionally, or alternatively, a diluent is added to the sampling module such as saline, physiological buffers such as PBS or Ringer's solution, cell culture medium, blood plasma or lymphatic fluid, and the like. While in one embodiment, the sampling module comprises anticoagulants and/or diluents which have been placed within the sampling module prior to initiation of the sampling process (e.g., for example, within a collecting chamber), in another embodiment, anticoagulents and/or diluents may be added to the sampling module, e.g., through one or more sample intake ports in communication with one or more chambers of the device.

In one embodiment, the sampling module includes a collection device, such as a sterile blood collection device as is known in the art. For example, in one embodiment, the collection device comprises a container for the collection of blood into a dedicated low volume blood bag (e.g., a 20 ml blood bag). Such bags are used routinely by Blood Services for 450 ml collections. The bag should be sterile and may contain a small quantity of anticoagulant (e.g., in a 7:1 ratio).

In one embodiment, the bag is further equipped with a needle, such as a 16 gauge needle. The collection device may additionally comprise one or more sampling ports (e.g., suitable for a Becton-Dickenson Vacutainer) from which to obtain small samples of fluid passing through the collection device for testing and cross-matching purposes. In one embodiment, the collection device further includes a septum to allow the device to interface with other components.

In one embodiment, the collection device is detachable from the sampling module for collection offsite and away from the sampling module itself. Thus, in one embodiment, dedicated vacutainers (such as supplied by Terumo Corporation, Tokyo Japan) are employed as collection devices. Such vacutainers are amenable to centrifugation, enabling a user of the system to centrifuge a source of cells for subsequent removal of the buffy-coat and plasma, leaving purified red cells. In this embodiment, the user is able to aspirate a known volume of red blood cells from the collection device for further manipulation, e.g., such for processing by a processing device.

In other embodiments, the sampling module comprises a plurality of blood bags with filters, which are fluidly connected, such as described, for example, in U.S. Pat. Nos. 4,596,657, 4,767,541, 4,810,378, and 4,855,063, the entireties of which are incorporated by reference herein. In still further embodiments, the sampling module comprises a plurality of chambers which individually collect, separate, buffer and/or transfer cells from a source; the chambers being connected by flow control mechanisms, such as described in, for example, RE Pat. No. 35,804, the entirety of which is incorporated by reference herein. In still further embodiments, the sampling module comprises separation elements, such as filtration elements and/or centrifugation mechanisms, for isolating red blood cells from other components of a source material.

In a further embodiment, the sampling module includes a separation device whose orientation with respect to a collection device is such that cells which flow into the separation device from the collection device are separated through the action of gravity. In one embodiment, this is facilitated by providing solutions within the separation chamber comprising different densities. In further embodiments, additional separation elements may be provided in communication with the separation device (e.g., such as filters, centrifugation mechanisms, and the like). In one embodiment, the separation device and the collection device are separable from one another, while maintaining a closed system.

In another embodiment, the sampling module comprises magnetic beads or microbeads coated with a molecule(s) suitable for specifically binding to a cell of interest with a source fluid. For example, in one embodiment, magnetic beads or microbeads are coated with an antibody or other binding moiety capable of specifically binding to an erythrocyte antigen, such as a molecule present on the surface of a red blood cell. Blood introduced into the collection device may be transferred to the separation chamber comprising the magnetic beads/microbeads and a magnetic field is applied to separate beads to which red blood cells are bound from other components. Alternatively, the beads may be provided within the collection device, and the collection device may be transformed into a separation device through the application of a magnetic field. Magnetic separation of red blood cells is described in detail in U.S. Pat. Nos. 4,910,148, 5,514,340, 5,567,326, 5,541,072, 4,988,618, 4,935,147, 6,132,607, 6,129,848 and 6,036,857, the entireties of which are incorporated by reference herein.

In highly preferred embodiments of the invention, the collection device comprises a selfcontained module, which may be disposable. This allows all manipulation to be carried out in a closed (or functionally closed system). In one embodiment, the functionally closed system is provided within a kit and is isolated from the environment by, for example, the presence of microbial filters to render it essentially sterile. The closed system may comprise solutions or other required components for separating, purifying, or buffering cells.

Resealing Module

The term "resealing" encompasses the stabilization of the membrane of a red blood cell by closing pores in the membrane that have previously been opened by some other process, for example, by a loading process such as hypotonic dialysis. In one embodiment, resealing is part of the loading procedure. However, in another embodiment, the loading system comprises a separate module in which resealing of cells takes place.

Resealing may be facilitated by suspending the cells in suitable resealing solution for a period of time. In one embodiment, a resealing module generally comprises any mechanism for bringing cells into contact with a suitable resealing buffer. In one embodiment, a resealing module comprises a chamber which is capable of holding a suitable resealing medium, in which cells which have been loaded are suspended. In another embodiment, the resealing module comprises temperature control elements for maintaining a desired temperature. In one embodiment, the resealing module comprises a stirrer, or any other mechanism for agitating cells to facilitate resealing.

It will be appreciated that resealing may suitably take place within the loading module, the sensitisation module and/or the pre-sensitisation module. Thus, the buffer within any, or all of these modules, may be exchanged with a suitable resealing medium. Thus, in some embodiments of the invention, the resealing mechanism may be a part of the loading module, the sensitisation module, and/or the pre-sensitisation module (i.e., the resealing mechanism may be integral with each, or all of these modules).

The resealing solution may be chosen from a group that includes, but is not limited to, physiological strength saline (i.e., isotonic saline), physiological buffers such as PBS or Ringer's solution, cell culture medium, and blood plasma or lymphatic fluid. Each of these may optionally comprise $Mg^{++}$ ions or glucose, for example, at 10 mM. The solutions may be provided as concentrates and diluted before use.

Washing Module

In one embodiment, the loading system is capable of removing unwanted material from a solution of cells, such as red blood cells. Typically, the unwanted material is one which is present in the medium in which the cells are suspended. For example, such unwanted material may include salts, sugars, nucleic acids, polypeptides, urea, etc. The unwanted material may include, but not be limited to, lysed cells or excess agent. A particular material which may be desirably removed is haemoglobin, which may be released from red blood cells during a loading procedure.

The unwanted material may be removed by washing the cells in a solution such as physiological strength saline (e.g., isotonic saline), and physiological buffers such as PBS or Ringer's solution. In one embodiment, washing is performed in a separate washing module within the system.

The washing module may include a mechanism for separating washing buffer from cells. For example, in one embodiment, the washing module comprises a centrifuge, one or more dialysis membranes, a column, a filter, or combinations thereof. In another embodiment, the washing module may comprise a mechanism for pulsed membrane filtration, or spinning membrane filtration. Other means of separation of cells from washing medium, such as magnetic separation, are known in the art, and are encompassed within the scope of the invention.

Monitoring Module

The fluid passing through any components of the loading system (e.g., the sampling module, pre-sensitisation module, loading module, sensitisation module, etc.) may be monitored to determine its composition. Any constituent of the fluid may be measured, but of particular interest are measurements of components which provide a measure of the loading efficiency of the system, i.e., those that provide an indication of the amount of agent that has been loaded into the cells. Therefore, in one embodiment, a monitoring module may be included in the system to enable such measurements to be made.

The monitoring module may measure the composition of the fluid by "destructive," or by "non-destructive" methods. An example of the former is direct sampling. For example, a sample of cells may be taken from the system, lysed, and the amount of agent loaded is measured directly. Examples of non-destructive monitoring module include, but not limited to, chemical, spectroscopic, spectrophotometric, fluorometric, light scattering, pH, and conductivity measurements. Monitoring may be done by any suitable method or using any suitable sensor mechanism capable of obtaining a desired measurement, depending on the nature of the agent to be measured.

In one embodiment, a monitoring module that is an integral part of the system is used to monitor the fluid composition in various modules of the device. The monitoring module may be positioned within the system so that fluid flows through, past, or in contact with the monitoring module. Measurements made by light, for example, light scattering, spectrophotometry and spectroscopy are particularly suited where the monitoring module is an integral part of the system. If the total amount of agent added to a solution of cells is known, then by measuring the amount of agent remaining outside the cells after loading provides a measurement of the amount of agent that has been loaded into the cells, enabling an assessment of loading efficiency to be made.

A further variable which may usefully be monitored is the number or percentage of cells (e.g., red blood cells) which survive the various processing stages carried out by the system. To monitor this quantity, lysed cells may be measured, for example, in the case of red blood cells, using a conventional haemolysis detector. Heamolysis measurements may be conducted by means known in the art, for example, by spectrophotometric measurement of soluble haemoglobin concentration, scattering, etc. The haemolysis detector may be placed in the system in communication with one or all of the various modules that make up the system. For example, a haemolysis detector may be placed after the sensitisation module, pre-sensitisation module, or the loading module. Alternatively, a sample may be taken from one or more modules in the system at any point for analysis by a haemolysis detector off-line.

The loading system may further comprise a feedback mechanism, such that any measurements that are made by a monitoring module may be used as a basis for adjusting the operating parameters of various modules of the system. The adjustment may be made manually, for example, by manipulating the controls of a pulse generator or by turning a valve controlling the amount of a material entering or leaving the system. For an on-line monitoring module, an electrical signal corresponding to a measurement may be fed to a pulse generator, or to valves controlling the flow of material into and out of the system, thereby forming a feedback system. In one embodiment, the electrical signal from an on-line monitoring device is fed into a computer or microprocessor or otherwise communication to a server for processing. The computer, microprocessor, or server, would then send a resultant electrical signal to, for example, the pulse generator or to valves controlling flow of material within the device.

Connecting Elements

In one embodiment, two or more of the modules of the loading system are in fluid connection with each other, such that fluid is capable of flowing from one module to at least one other module, either continuously or discontinuously. In one embodiment, the flow of materials into and out of the modules is controlled by valves. The valves may be of any design suitable to control the flow of material. Examples include, but are not limited to, manual valves, pneumatic valves, mass flow controllers, needle valves and solenoid valves. Preferably, at least some of the various modules present in the invention are electrically isolated from each other. This is important where products of any of the various steps which may include use of an electric field (for example, pre-sensitisation, sensitisation, etc) are delivered directly into a patient. Electrical isolation of the relevant modules from the patient thus minimizes the risk of electric shock to the patient. Electrical isolation may be achieved by the use of suitable insulated valves, as are known in the art. In additional embodiments, one or more modules are in communication with each other through the use of drip feeds, where fluid from one module or part of the system drips onto a receiving container included within a module, for example, under the influence of gravity, or negative pressure.

Control Module

In one embodiment, the loading system is in communication with a control module comprising one or more computers or other processors capable of executing programmed instructions. The software for the control module may be provided in read-only format (ROM), or may be re-programmed by storage in RAM, or external devices such as floppy discs, hard discs, CD-ROMs, flash-ROMs, etc. The control module may include a keyboard or other input device for programming, or otherwise controlling the system. A computer or processor to which the system is linked may also be in communication with the network. The system may have a manual override, which may be in the form of control knobs, or alternatively, overrides may be in the form of keyboard input. The computers and processors included within the system are preferably programmable or comprise some other mechanism to optimize the parameters of the various modules included within the system. Preferably, the system is capable of acting under instructions from a microprocessor without the need for user intervention.

Agents

A variety of different agents may be loaded into cells using the system of the present invention. Preferred agents include those useful for imaging of tissues in vivo or ex vivo. For example, imaging agents, such as antibodies which are specific for defined molecules, tissues or cells in an organism, may be used to image specific parts of the body by releasing delivery vehicles prepared using the loading system at a desired location using ultrasound. This allows imaging agents which are not completely specific for the desired target, and which might otherwise lead to more general imaging throughout the organism, to be used to image defined tissues or structures. For example, in one embodiment, an antibody which is capable of imaging endothelial tissue is used to image endothelial cells in lower body vasculature, such as in the lower limbs, by releasing the antibody selectively in the lower body by applying ultrasound energy thereto. The ultrasound energy will preferentially lyse the delivery vehicles prepared using the loading system, thereby achieving selective therapeutic effects with minimal damage to normal cells.

An agent may be in solution or in suspension (e.g., in crystalline, colloidal or other particulate form). The agent may be in the form of a monomer, dimer, oligomer, etc, or otherwise in a complex. The agent may be coated with one or more molecules, preferably macromoleucles, most preferably polymers such as PEG (polyethylene glycol). Use of a PEGylated agent increases the circulating lifetime of the agent once released.

The agent may be an imaging agent, by which term is meant an agent which may be detected, whether in vitro or in vivo in the context of a tissue, organ or organism in which the agent is located. In one embodiment, the imaging agent emits a detectable signal, such as light or other electromagnetic radiation. In another embodiment, the imaging agent is a radio-isotope, for example $^{32}$P or $^{35}$S or $^{99}$Tc, or a molecule such as a nucleic acid, polypeptide, or other molecule, conjugated with such a radio-isotope. In one embodiment, the imaging agent is opaque to radiation, such as X-ray radiation. In another embodiment, the imaging agent comprises a targeting functionality by which it is directed to a particular cell, tissue, organ or other compartment within the body of an animal. For example, the agent may comprise a radiolabelled antibody which specifically binds to defined molecule(s), tissue(s) or cell(s) in an organism.

The imaging agent may be combined with, conjugated to, mixed with, or combined with, any of the agents disclosed herein.

It will be appreciated that it is not necessary for a single agent to be used, and that it is possible to load two or more agents into a cell. Accordingly, the term "agent" also includes mixtures, fusions, combinations and conjugates, of atoms, molecules etc as disclosed herein. For example, an agent may include, but is not limited to, a nucleic acid combined with a polypeptide; two or more polypeptides conjugated to each other; a protein conjugated to a biologically active molecule (which may be a small molecule such as a prodrug); or a combination of a biologically active molecule with an imaging agent.

In another embodiment, the agent is a biological effector molecule which has activity in a biological system. Biological effector molecules according to the invention, include, but are not limited to, a protein, polypeptide, or peptide, including, but not limited to, a structural protein, an enzyme, a cytokine (such as an interferon and/or an interleukin), an antibiotic, a polyclonal or monoclonal antibody, or an effective part thereof, such as an Fv fragment, which antibody or part thereof, may be natural, synthetic or humanised, a peptide hormone, a receptor, or a signalling molecule. Included within the term "immunoglobulin" are intact immunoglobulins as well as antibody fragments such as Fv, a single chain Fv (scFv), a Fab or a F(ab')$_2$.

Preferred immunoglobulins, antibodies, Fv fragments, etc, are those which are capable of binding to antigens in an intracellular environment, known as "intrabodies" or "intracellular antibodies." An "intracellular antibody" or an "intrabody" is an antibody which is capable of binding to its target or cognate antigen within the environment of a cell, or in an environment which mimics an environment within the cell.

Selection methods for directly identifying such "intrabodies" include the use of an in vivo two-hybrid system for selecting antibodies with the ability to bind to antigens inside mammalian cells. Such methods are described in International Patent Application number PCT/GB00/00876, incorporated herein by reference. Techniques for producing intracellular antibodies, such as anti-β-galactosidase scFvs, have also been described in Martineau, et al., 1998, *J Mol Biol* 280, 117–127 and Visintin, et al., 1999, *Proc. Natl. Acad. Sci. USA* 96, 11723–11728, the entireties of which are incorporated herein.

Preferably the biological effector molecule is selected from the group consisting of a protein, a polypeptide, a peptide, a nucleic acid, a virus, a virus-like an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

A biological effector molecule may include a nucleic acid, including, but not limited to, an oligonucleotide or modified oligonucleotide, an antisense oligonucleotide or modified antisense oligonucleotide, an aptamer, a cDNA, genomic DNA, an artificial or natural chromosome (e.g. a yeast artificial chromosome) or a part thereof, RNA, including MRNA, tRNA, rRNA or a ribozyme, or a peptide nucleic acid (PNA); a virus or virus-like particles; a nucleotide or ribonucleotide or synthetic analogue thereof, which may be modified or unmodified. In a preferred embodiment of the invention, the loading system is adapted for use in loading a ribozyme or an oligonucleotide, such as an antisense oligonucleotide, into a red blood cell, which is optionally sensitised, for delivery into a target cell or tissue.

The biological effector molecule can also be an amino acid or analogue thereof, which may be modified or unmodified or a non-peptide (e.g., steroid) hormone; a proteoglycan; a lipid; or a carbohydrate.

If the biological effector molecule is a polypeptide, it can be loaded directly into a cell of the invention, such as a red blood cell; alternatively, a nucleic acid molecule bearing a sequence encoding a polypeptide, which sequence is operatively linked to transcriptional and translational regulatory elements active in a cell at a target site, may be loaded. Small molecules, including inorganic and organic chemicals, are also of use in the present invention. In a particularly preferred embodiment of the invention, the biologically active molecule is a pharmaceutically active agent, for example, an isotope.

Particularly useful classes of biological effector molecules include, but are not limited to, antibiotics, anti-inflammatory drugs, angiogenic or vasoactive agents, growth factors and cytotoxic agents (e.g., tumour suppressers). Cytotoxic agents of use in the invention include, but are not limited to, diptheria toxin, Pseudomonas exotoxin, cholera toxin, pertussis toxin, and the prodrugs peptidyl-p-phenylenediamine-mustard, benzoic acid mustard glutamates, ganciclovir, 6-methoxypurine arabinonucleoside (araM), 5-fluorocytosine, glucose, hypoxanthine, methotrexate-alanine, N-[4-(a-D-galactopyranosyl) benyloxycarbonyl]-daunorubicin, amygdalin, azobenzene mustards, glutamyl p-phenylenediamine mustard, phenolmustard-glucuronide, epirubicin-glucuronide, vinca-cephalosporin,phenylenediamine mustard-cephalosporin, nitrogen-mustard-cephalosporin, phenolmustard phosphate, doxorubicin phosphate, mitomycin phosphate, etoposide phosphate, palytoxin-4-hydroxyphenyl-acetamide, doxorubicin-phenoxyacetamide, melphalan-phenoxyacetamide, cyclophosphamide, ifosfamide or analogues thereof.

If a prodrug is loaded in an inactive form, a second biological effector molecule may be loaded into a cell of the present invention. Such a second biological effector molecule is usefully an activating polypeptide which converts the inactive prodrug to active drug form. In one embodiment, activating polypeptides include, but are not limited to, viral thymidine kinase (encoded by Genbank Accession No. J02224), carboxypeptidase A (encoded by Genbank Accession No. M27717), α-galactosidase (encoded by Genbank Accession No. M13571), β-gluucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase, or penicillin amidase.

Either the polypeptide or the gene encoding it may be loaded into cells of the present invention; if the latter, both the prodrug and the activating polypeptide may be encoded by genes on the same recombinant nucleic acid construct. Furthermore, either the prodrug or the activator of the prodrug may be transgenically expressed and already loaded into the red blood cell according to the invention. The relevant activator or prodrug (as the case may be) is then loaded as a second agent according to the methods described herein.

Methods of Generating Delivery Vehicles

The invention further provides a method for providing a cell suitable for delivery of an agent to a vertebrate, the method comprising the steps of: providing a loading system as described above, in any of the embodiments described above, loading the cell with an agent in the loading module of the system; and sensitising the cell in the sensitising module of the system. In one embodiment, the cell is a red blood cell.

In one embodiment, the method further comprises pre-sensitising the cells in a presensitising module of the system. Either or both, sensitisation or pre-sensitisation may be performed using an electroporator. In another embodiment, the method comprises the step of sampling a source of cells, to perform one or more of collecting, separating, and processing, the cells for pre-sensitisation and/or loading and/or sensitisation. In still another embodiment, the method comprises the step of resealing cells, after any of: pre-sensitisation, loading, and/or sensitisation. In a further embodiment, the method comprises the step of washing cells to remove debris and/or other undesired components. In still a further embodiment, various stages of the method are monitored, to observe the efficacy of loading the cell with the agent. In one embodiment, the method comprises providing a delivery vehicle for delivering an imaging agent and/or a biological effector molecule. In one embodiment the biological effector molecule is a drug. In another embodiment, the biological effector molecule is a toxic molecule.

EXAMPLE

Figure 1:
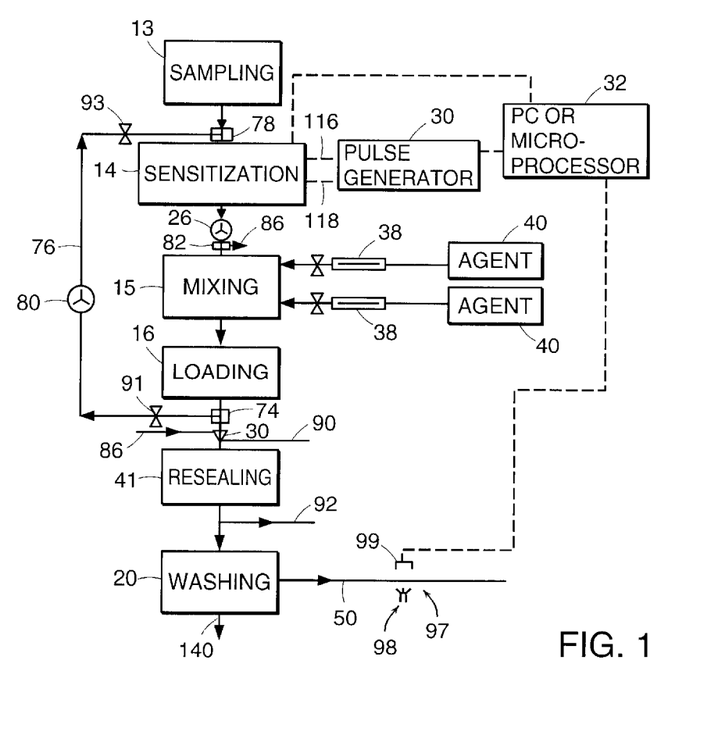
FIG. 1 shows a schematic diagram for a system according to a first embodiment of the invention, comprising a sensitisation module and a loading module, and a device according to a fourth embodiment of the invention, which comprises a pre-sensitisation/sensitisation module and a loading module.

A schematic diagram of an system according to one embodiment of the invention is shown in FIG. 1. The system comprises a sensitisation module and a loading module which are in fluid connection with each other. The connections between the various parts of the system, as described hereafter, may be by suitable IV tubing segments which are represented in the Figures by single solid lines. Arrows on the single solid lines represent the direction of fluid flow through the IV tubing.

The sensitisation module 14 may comprise a temperature-controlled housing containing one or more means which are designed to impart an electrical field to cells, such as red blood cells that flow through the sensitisation module 14. The temperature-controlled housing may be maintained at a temperature that is either pre-set, set by a user, or set according to instructions from a microprocessor/computer 32. The cells (optionally from a sampling module, as described below) flow into the sensitisation module 14 by gravity feed or under the influence of a peristaltic pump.

Figure 3:
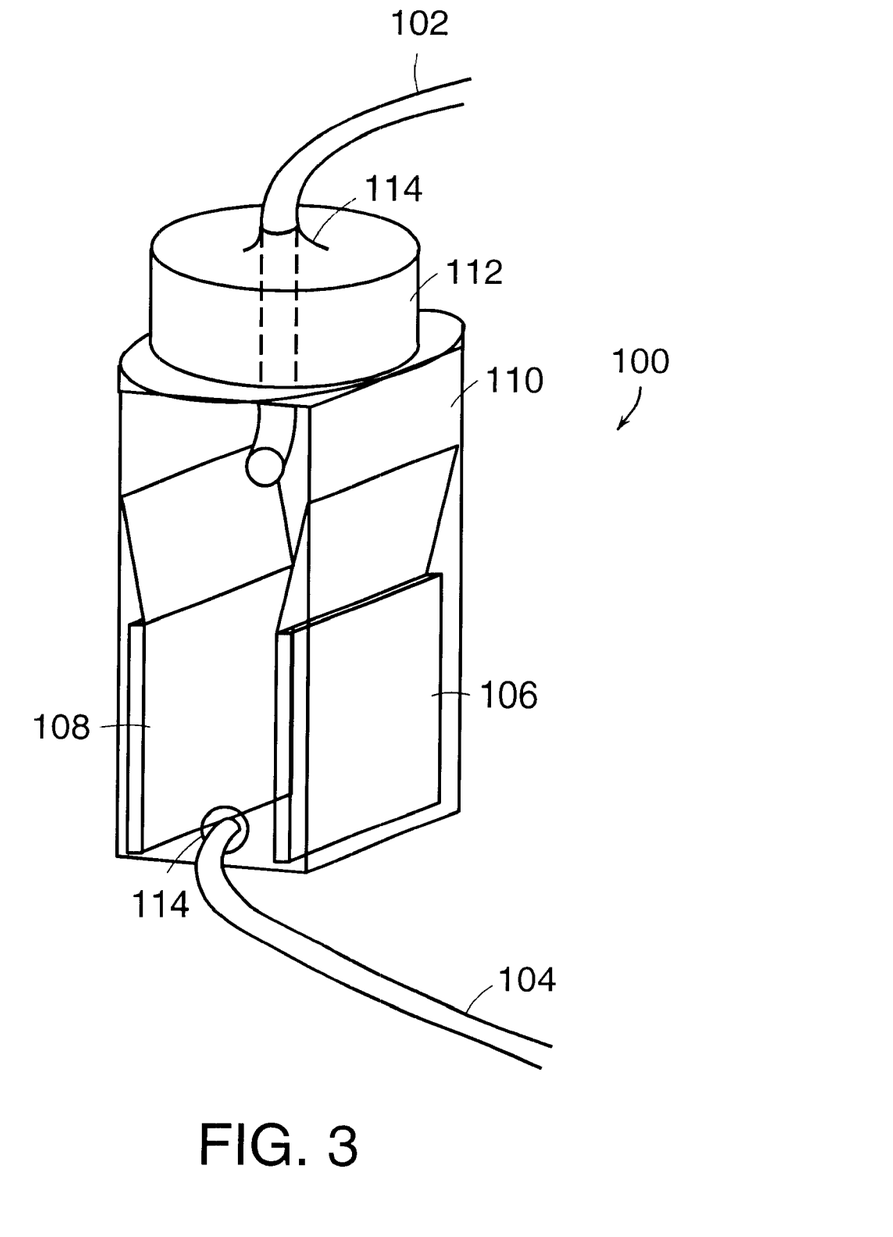
FIG. 3 shows a schematic diagram of a flow through cuvette for use in the invention.

In a first example, the sensitisation module 14 comprises one or more flow-through cuvettes 100, which may be disposable. An illustration of a flow-through cuvette 100 is shown in FIG. 3. The cuvette chamber comprises a clear plastic rectangular housing defining an enclosure 110 having a opening at the upper end. A push-on cap 112 closes this opening. A tubing segment 102 extends snugly through a hole in the middle of the cap 112 that is sealed with a fitting 114. The end of the tubing segment 102 acts as an inlet for the cells into the cuvette 100. Tubing section 104 extends snugly through a hole situated at or near the bottom of the cuvette 100 and the hole is sealed with a fitting 114. The tubing section 104 acts as an outlet for the cells. The enclosure 110 is preferably moulded with a pair of embedded elongated electrodes 106 and 108 which are connected to cables 116 and 118 (shown in FIG. 1) that receive an electrical signal from a pulse generator 30. The electrodes 106 and 108 are uniformly spaced apart and extend parallel, substantially along the full length of the chamber, between the inlet and outlet to enable fluid to pass therebetween. The electrodes may be of any suitable conductive material such as stainless steel or aluminum and may be gold or platinum plated where desired. The electrodes may be disposable. Various profiles for the electrodes are possible, for example, crenellated, sinuous, etc. Such profiled electrodes have the advantage of increased electrode surface area, leading to more even field strength.

In a second example of the first embodiment the sensitisation module comprise a series of micropores. Each micropore comprises a tubular member or pore with electrodes positioned on either side. The electrodes are uniformly spaced apart and extend parallel, substantially the full length of the pore, between an inlet and an outlet to enable fluid to pass through the pore. The electrodes may comprise two concentric circular electrodes with fluid directed to flow between the electrodes. The gap between the electrodes is generally less than the gap between the electrodes of a flow-through cuvette. The electrode gap may be adjusted and for a particular voltage applied to the electrodes, the smaller the electrode gap the larger the electric field exerted on the cells that pass between the electrodes. By way of example only, an applied voltage of only 3.6 V and an electrode separation of 10 $\mu$m results in electric field of 3.6 kV/cm, which is an electric field strength that is capable of readily sensitising red blood cells. It will be appreciated that the use of micropores requires a low voltage and is especially amenable for use in a portable or battery operated device.

Different electrode gaps may be chosen according to the particular flow rate and protocol required by a user of the system. The electrodes are connected to the pulse generator 30 by cables 116 and 118.

The pulse generator 30 (FIG. 1) is connected to a mains supply and provides electrical pulses to the electrodes of the sensitisation module 14 via the electrical cables 116 and 118. An exemplary pulse generator 30 is the Electro Cell Manipulator Model ECM 600R commercially available from Gentronics Inc., of San Diego, Calif., U.S.A. A BTX ECM630 electroporator may also be used. Another pulse generator which may be used is a Gene Pulser I or II, made by Biorad.

The pulse generator 30 may be controlled manually to deliver one or more pulses that have particular parameters. The parameters include the peak voltage, waveform, duration and frequency of the pulses and the duration and duty cycle of the pulse train. The pulse generator 30 is preferentially controlled by the microprocessor/computer 32. The microprocessor/computer 32 may be pre-programmed to control the pulse generator 30 to give a train of pulses with a particular set of parameters. Alternatively the microprocessor/computer 32 may be configured to allow a user to enter the parameters of the pulse train via an interactive touch sensitive screen.

The cells are fed from the sensitisation module 14 via a peristaltic pump 26 into a mixing means comprising a mixing chamber 15. Agents 40, are pumped into the mixing chamber 15 by one or more injection pumps 38. The agents 40 are in the form of dedicated IV packs containing a drug in an isotonic saline solution. The fluid containing the red blood cells and the agents 40 is then fed into a loading module 16. It will be appreciated that mixing may take place within the loading module, so that the use of a separate mixing means is obviated. In this embodiment, the agents are fed into the loading module and mixed with the red blood cells within the chamber.

The loading module 16 may comprise one or more conventional dialysis devices. A number of dialysis devices are known in the art and are commercially available. A general dialysis device may comprise a semipermeable membrane. The semipermeable membrane comprises pores; molecules having dimensions greater than the pore diameter remain within the dialysis device whereas smaller molecules traverse the pores and emerge in the dialysate outside the dialysis device. The membrane may be composed of for example, but not limited to, cellulose acetate, polyethylene and polypropylene. As described above, the red blood cells may be suspended inside a suitably sealed dialysis tubing, and exposed to external medium to accomplish hypotonic dialysis.

Alternatively, and as described above, the loading module 16 may comprise one or more hollow fibers. If a small number of cells are required to be loaded then one or more single hollow fibers such as Spectra/Por hollow fibers as supplied by Spectrum Laboratories may be used. If a large number of cells are required to be loaded, then a hollow fiber cartridge which comprises a plurality of hollow fibers may be used. The number of hollow fibers within a hollow fiber cartridge is dependent on the throughput requirements of the user of the system. An exemplary hollow fiber cartridge is one supplied by Serotec. Loading by hypotonic dialysis of the cells with the agent takes place in the hollow fibers and the hollow fiber cartridges. The loading module may further comprise means for regulating the flow of medium past the hollow fiber(s), as well as means for agitating the loading module to accomplish mixing.

For safety purposes, the system can also include a bar-code reader to read the bar-codes on, for example, supplies of blood cells and/or drugs and/or other agents to ensure the integrity of those supplies.

Figure 2:
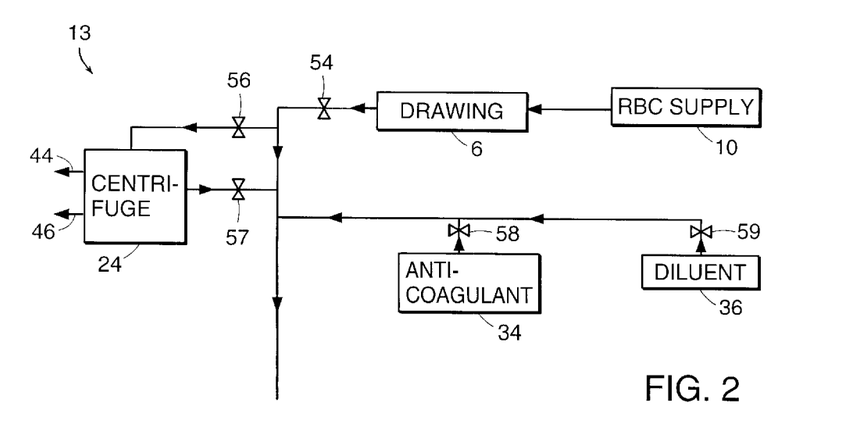
FIG. 2 shows a schematic diagram of a preferred embodiment of a sampling module for use in the invention.

Optionally, the system further comprises a sampling module 13. The sampling module provides a solution of cells, such as red blood cells, that is suitable to pass into the sensitisation module 14. An exemplary sampling module 13 is shown in FIG. 2 and comprises a supply of red blood cells 10, a drawing element 6, a centrifuge 24, an anti-coagulant reservoir 34, and a diluent reservoir 36. The blood supply 10 may be a bag or tube, optionally direct from a patient. The drawing element 6 receives red blood cells from the supply 10 of either whole blood or of red blood cells (which may be packed cells suspended in a buffer solution). The drawing element 6 is preferentially a sterile tube welder or a sterile docking means. The sterile docking element may be one that is commercially available, for example one as supplied by Terumo. In certain embodiments, the supply of whole blood may come directly from a patient, in which case the drawing element 6 is adapted to receive blood directly from the veins and/or arteries of a patient and may include, for example, a sterile needle.

For a supply 10 that comprises whole blood, the blood flows from the drawing element 6 into a centrifuge 24. The centrifuge 24 is connected parallel to the IV tubing that leads from the drawing element 6 by two T-shaped couplings (not shown). Solenoid valves 56 and 57 control whether or not blood from the supply 10 flows through the centrifuge 24. The centrifuge 24 separates the red blood cells from the white blood cells and other components in the whole blood. The white blood cells exit the centrifuge 24 through an outlet 44 and may be stored or discarded. Other waste materials from the whole blood exit the centrifuge 24 through an outlet 46 and may be discarded. A single outlet may be used for both white blood cells and other waste materials (i.e., outlets 44 and 46 may be combined).

The red blood cells, which may come from the centrifuge 24 or directly from the drawing element 6 (in the case of ready prepared red blood cells), may be diluted with a diluent from the diluent reservoir 36. If the red blood cells come from a supply that does not contain an anticoagulant, the cells are mixed with an anti-coagulant from the anticoagulant reservoir 34. The flow from the drawing element 6, the anti-coagulant reservoir 34 and the diluent reservoir 36 is controlled by solenoid valves 59 which in turn are controlled electronically by a microprocessor/computer 32.

Resealing of the red blood cells after loading by hypotonic dialysis may take place within the loading module by suitable buffer exchange, or via a separate resealing module, as described in detail above. An exemplary resealing module 41 is described here. The cells are fed from the loading module 16 into the resealing module 4, which comprises a vessel in which the red blood cells are mixed with a resealing buffer from a resealing buffer reservoir (not shown). The resealing buffer may comprise a salt solution, exemplary salt solutions including PBS containing $MgCl_2$ (for example at 4 mM) (PBS/Mg). Other examples of resealing buffers are known in the art, and are described in for example U.S. Pat. No. 6,074,605, the entirety of which is incorporated by reference herein; however, any buffer suitable for resealing may be used. The resealing module 41 retains the cells at a set temperature for set period of time. By way of example the cells may be incubated at room temperature for at least 30 min in the resealing buffer at a concentration of $7 \times 10^8$ cells/ml. However, the temperature, retention period, and cell concentration may be set to be many different combination of values for optimal resealing as determined by the user of the system. The system comprises a connection 90, in the IV tubing connecting the loading module 16 to the resealing module 41. The connection 90 enables an option of removing the fluid containing the red blood cells from the system for re-sealing off-line.

Optionally, the system further comprises a washing module 20 in fluid connection with the resealing module 41. The washing module 20 comprises a vessel that mixes the red blood cells with a washing buffer from a washing buffer reservoir (not shown). The washing buffer may comprise a salt solution, by way of example only, the washing buffer may be PBS/Mg containing 10 mM glucose (PBS/Mg/glucose). However any buffer suitable for the washing the cells may be used. The supernatant is removed from the washing module 20 via a waste outlet 50. Optionally, cells are subsequently suspended for a period of time. The cells may, for example, be suspended at a concentration of $7 \times 10^8$ cells/ml for at least 1 hour. However, the concentration and period of suspension may be varied according to a particular protocol set by the user of the system. Washing may also appropriately be done during or after loading or resealing of the red blood cells, as lysis of the red blood cells can take place during loading, and accordingly the loading system may comprise connecting elements to connect the loading module to the washing module for this purpose (not shown).

The washing module 20 where present may comprise any commercial available washing device as known in the art, such as those described in, for example, U.S. Pat. No. 6,074,605, the entirety of which is incorporated by reference herein. The system may have a connection 92 in the IV tubing connecting the resealing module 41 to the washing module 20. The connection 92 provides an option of removing the fluid containing the red blood cells from the system for washing off-line (i.e., outside the system).

Optionally, the system comprises a monitoring module 97, through which the supernatant in outlet 50 passes. The monitoring module 97 monitors the amount of agent in the supernatant by spectrophotometry, for example. The amount of agent that is in the supernatant provides a measure of the amount of agent that has been loaded into the red blood cells. The monitoring module 97 comprises a light source 98 capable of emitting light of a suitable wavelength and a photodetector 99. The photodetector 99 generates a signal that varies in response to the amount of agent in the supernatant. The signal is fed from the photodetector 99 to the microprocessor/computer 32, which responds to the signal by adjusting the operating parameters of the system. The operating parameters could comprise, for example, the operating parameters of the pulse generator 30. The monitoring module 97, microprocessor/computer 32 and signal generator 30 therefore form part of a feedback system that regulates the amount of agent loaded into the cells.

After exiting the washing module 20, the red blood cells may either be re-suspended in a suitable buffer, for example, Sag-M and may enter directly into a patient via a port 140 (if the red blood cells are autologous) or stored for future use in a bar-coded pack containing Sag-M that is connected to port 140. The bar-coded pack contains a small sampling pack for cross matching and quality control purposes.

As noted above, sensitisation may occur before or after loading; accordingly, the sensitisation module and the loading module may be connected in either order.

Figure 4:
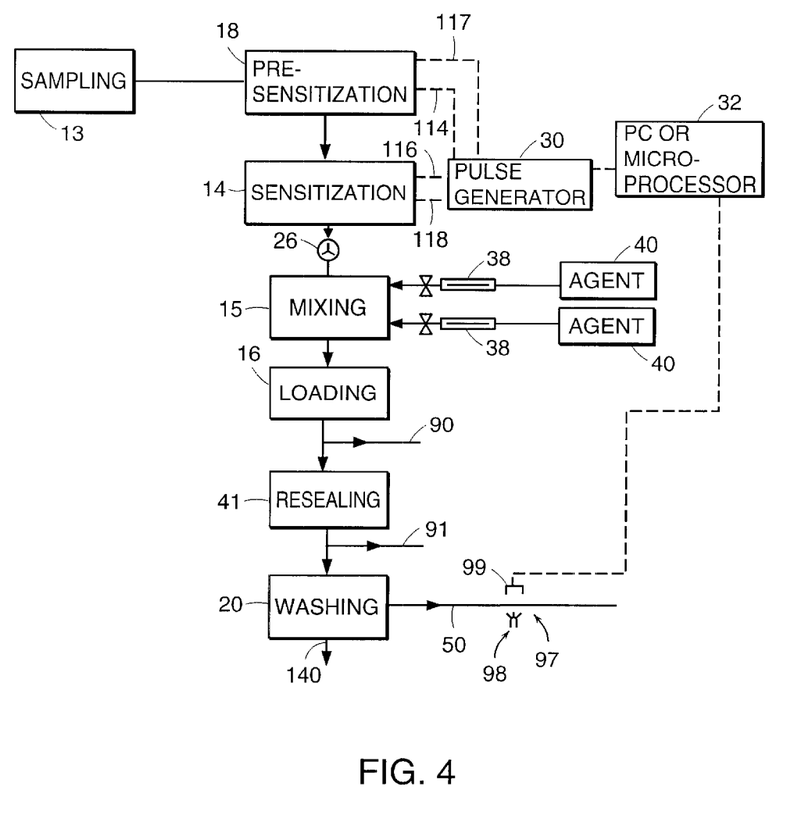
FIG. 4 shows a schematic diagram of a system according to a second embodiment of the invention.

FIG. 4 illustrates an system according to another embodiment of the invention. The system comprises a pre-sensitisation module 18, a sensitisation module 14 and a loading module 16.

The pre-sensitisation module 18 comprises a temperature-controlled housing and one or more elements designed to impart an electrical field on the cells that flow through the presensitisation module 18. The temperature-controlled housing is maintained at a temperature that is either pre-set, set by a user, or set according to instructions from a microprocessor/computer 32. The pre-sensitisation module 18 may comprise one or more disposable flow-through cuvettes 100, and/or one or more micropores, each of which are described above. A pulse generator 30 is connected to a mains supply and provides electrical pulses to the pre-sensitisation module 14 via electrical cables 117 and 119. The pulse generator 30 may have the same construction as that described above. The pulse generator 30 is preferentially controlled by a microprocessor/computer 32 of the same construction as that described above.

Cells are fed from the pre-sensitisation module 18 into a sensitisation module 14 which may have the same construction as those described previously. The pulse generator 30, supplies electrical pulses to the electrodes of the sensitisation module 14 via the electrical cables 116 and 118. Cells may be fed from the sensitisation module 14 via a peristaltic pump 26 into an optional mixing chamber 15. One or more agents 40 are pumped into the mixing chamber 15 by one or more injection pumps 38. The fluid is then fed into the loading module 16 of the same construction as that described in the first embodiment.

Optionally, the system further comprises a sampling module 13 having the same construction as that described above and/or resealing module 41. Optionally, the system further comprises a washing module 20 and/or monitoring module 97. The supernatant may be removed from the washing module 20 via a waste outlet 50 and through the monitoring module 97. The system may have ports 90 and 91 that allow the cells to be removed from the system and resealed and/or washed off-line.

Figure 5:
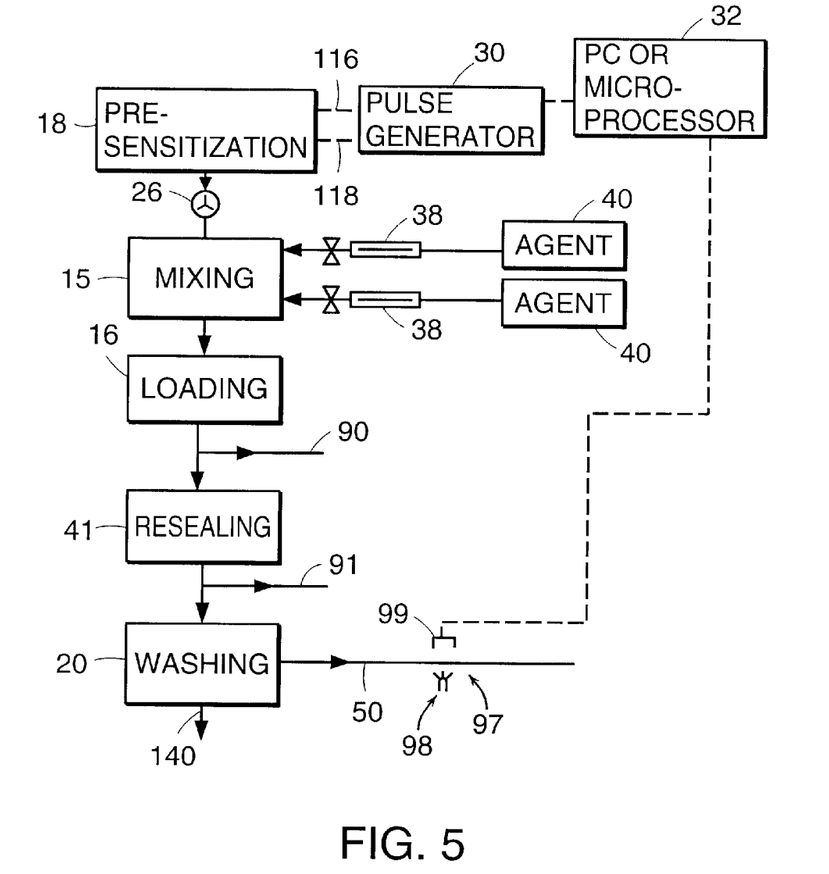
FIG. 5 shows a schematic diagram for a system according to a third embodiment of the invention.

FIG. 5 illustrates a system according a further embodiment of the invention. The system comprises a pre-sensitisation module 18 and a loading module 16. Cells flow from the pre-sensitisation module 18 into the loading module 16 via a segment of IV tubing. The presensitisation module 18, the loading module 16, and (where present, the mixing chamber 15) are of the same construction as those described in the previous embodiments. A system according to this embodiment may optionally comprise a sampling module 13, a resealing module 41, a washing module 20, a monitoring module, each as described previously. A system according to this embodiment is capable of loading cells, such as red blood cells, with agent at high efficiencies.

An system according to still another embodiment, comprises a sensitisation module 14 and a loading module 16. As shown in FIG. 1, the system can be constructed so that the red blood cells can pass through the sensitisation module 14 twice, as will be described in more detail below. In this embodiment, the sensitisation module is used to both pre-sensitize the cells, as well as to sensitize the cells. When the cells pass through the sensitisation module 14 for the first time, the sensitising means 14 acts to pre-sensitize the cells. When the cells pass through the sensitisation module 14 for a second time, the sensitising means acts to sensitize the cells. The sensitisation module 14 comprises a temperature-controlled housing and one or more means designed to expose the cells that flow through the sensitisation module 14 to an electric field. The temperature-controlled housing is maintained at a temperature that is either pre-set, set by a user, or set according to instructions from a microprocessor/computer 32. The sensitisation module may comprise one or more disposable flow-through cuvettes 100 and/or one or more micropores, as described above.

In one embodiment, a pulse generator 30 is connected to a mains supply and provides electrical pulses to the sensitisation module 14 via electrical cables 116 and 118. When cells enter the sensitisation module 14 for the first time (i.e., directly from sampling module 13), the PC/microprocessor 32 controls the pulse generator 30 so that signals to the sensitisation module 14 cause the sensitisation module to act to pre-sensitize the red blood cells. A peristaltic pump 26 connects the sensitisation module 14 to a mixing chamber 15. Cells are fed from the sensitisation module 14 via the peristaltic pump 26 into the mixing chamber 15. One or more agents 40 are pumped into the mixing chamber 15 by one or more injection pumps 38. The fluid is then fed into a loading module 16. Optionally, agents may be mixed with the cells in the loading module itself.

In one embodiment, the loading module 16 comprises cuvettes or hollow fiber cartridges 130. The IV tubing leading from the loading module 16 comprises a T-shaped coupling 74 that allows the cells to flow through an IV tubing segment 76 under the influence of a peristaltic pump 80. The IV tubing 76 is further connected via a T-shaped coupling 78 to the IV tubing leading into the sensitisation module 14. Cells flow through the IV tubing 76 and into the sensitisation module 14 for a second time. The T-shaped couplings 76 and 78 contain valves (not shown) that allow cells to flow only in the direction indicated above. The IV tubing 76 contains solenoid valves 91 and 93 that are operable to stop fluid flowing through the IV tubing segment 76 if the cells have passed through the sensitisation module 14 only once.

When cells enter the sensitisation module 14 via IV tubing 76 (i.e., the cells are entering the sensitisation module for a second time), the PC/microprocessor 32 controls the pulse generator 30 so that signals to the sensitisation module 14 cause the sensitisation module 14 to act to sensitize the red blood cells.

After passing through the sensitisation module 14 for the second time, the cells enter a T-shaped coupling 82 that enables the cells to flow through an IV tubing segment 86 (shown in part only). The IV tubing segment 86 is further connected to a T-shaped coupling 84 which is on the IV tubing leading from the loading module 16. The IV tubing segment 86 contains solenoid valves (not shown). The solenoid valves are operated by the PC/microprocessor 32 to allow cells to pass through the IV tubing segment 86. Therefore, when the cells have passed through the sensitisation module for a second time, the solenoid valves operate so that the cells by-pass the mixing chamber 15 and loading module 16.

In further embodiments, the system comprises a sampling module 13, and/or a resealing module 41, and/or a washing module 20, and/or a monitoring module, each as described previously.

Any or all of the various components of the system in its embodiments, such as the IV tubing, and the flow-through cuvettes 100, etc, are preferably made of easily sterilizable material, such as plastic or metal, etc. Such material may be sterilized by, for example, heat, autoclaving, ethylene oxide, gamma irradiation, electron beams, etc.

Alternatively, or in addition, one or more components of the system may be disposable. Thus, for example, a loading module comprising a cuvette may be made in a disposable form, for patient hygiene and safety. The components may be made and sold in disposable "sets", comprising for example, a cuvette for loading, a sensitisation chamber (optionally with any of the other components of the device) which may be swapped into the system for each use. The invention, thus further encompasses such kits and sets, and their use. Furthermore, the system according to the invention may be made and sold together with an ultrasound generating system, preferably a portable ultrasound generator, in order to effect disruption of sensitised (and optionally loaded) red blood cells. Ultrasound generators are known in the art.

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A system for providing a cell suitable for delivery of an agent to a vertebrate, the system comprising:
   (a) a loading module for loading a cell with an agent; and
   (b) a sensitisation module in fluid communication with said loading module, said sensitisation module for sensitising a cell to an energy field, such that said cell is induced to release the agent upon exposure to said energy field, and wherein said sensitisation module and said loading module are separate.

2. The system according to claim 1, wherein said loading module comprises a mechanism for loading said cell by hypotonic dialysis.

3. The system according to claim 1 or 2, wherein said loading module comprises one or more hollow fibers.

4. The system according to claim 1, further comprising a pre-sensitisation module for exposing a cell to a condition which increases the ability of a cell to be loaded in the loading module at least two-fold compared to a cell which is not pre-sensitised.

5. The system according to claim 4, in which the pre-sensitisation module and the sensitisation module are integral with each other.

6. The system according to claim 4, in which the pre-sensitisation module and the sensitisation module are separate.

7. The system according to claim 4, in which the pre-sensitisation module and the loading module are separate and are in fluid connection with each other.

8. The system according to claim 1, in which one or both of the sensitisation module and the pre-sensitisation module are in communication with a source of electrical energy.

9. The system according to claim 8, in which the sensitisation module comprises a chamber for receiving the cell, one or more walls of which are defined by electrodes to enable an electric field to be established within the chamber.

10. The system according to claim 9, in which at least one electrode has a crenellated or sinusoidal cross sectional profile.

11. The system according to claim 9 or 10, in which the sensitisation module comprises one or more flow-through cuvettes.

12. The system according to claim 9 or 10, in which the sensitisation module comprises one or more micropores.

13. The system according to claim 12, in which the micropore comprises electrodes positioned to define a space capable of allowing passage of a cell.

14. The system according to claim 13, wherein the cell is a red blood cell.

15. The system according to claim 13 or 14, wherein said electrodes are tubular.

16. The system according to claim 1 or 2, further comprising a resealing module for resealing the cell subsequent to loading.

17. The system according to claim 1, further comprising a monitoring module comprising a sensor for sensing the amount of agent which is loaded into the cell.

18. The system according to claim 17, further comprising a feedback mechanism adapted to receive a signal from the monitoring module and to altering one or more loading parameters to adjust the amount of agent loaded into the red blood cell.

19. A method for producing a cell suitable for delivery of an agent to a vertebrate, the method comprising the steps of:
   (a) placing a cell within the loading module of the system according to claim 1, and loading said cell with an agent; and
   (b) prior to, or after said loading, placing said cell within the sensitising module and sensitising the cell.

20. A method for producing a cell suitable for delivery of an agent to a vertebrate, the method comprising the steps of:
   (a) placing a cell within the pre-sensitising module of said system according to claim 4 and exposing said cell to the pre-sensitising condition,
   (b) placing the cell in the loading module of the system and loading said cell with an agent;
   wherein, prior to, or after said loading, said cell is placed within, and sensitised in the sensitising module.

21. The method of claim 19 or 20, wherein said sensitising comprises exposing said cells to an electrical pulse.

* * * * *

UNITED STATES PATENT AND TRADEMARK OFFICE
CERTIFICATE OF CORRECTION

PATENT NO.     : 6,495,351 B2
DATED          : December 17, 2002
INVENTOR(S)    : Anthony Patrick McHale It is certified that error appears in the above-identified patent and that said Letters Patent is hereby corrected as shown below:

<u>Title page,</u>
Item [63], Each occurrence of "continuation" should read -- continuation-in-part --

<u>Column 1,</u>
Line 5, of "continuation" should read -- continuation-in-part --

Signed and Sealed this

Seventh Day of October, 2003

JAMES E. ROGAN
*Director of the United States Patent and Trademark Office*